United States Patent [19]
Ehr et al.

[11] Patent Number: 5,706,827
[45] Date of Patent: Jan. 13, 1998

[54] MAGNETIC LUMEN CATHETER

[75] Inventors: Timothy G. J. Ehr, Elk River; David J. Blaeser, Champlin, both of Minn.

[73] Assignee: SciMed Life Systems, Inc., Maple Grove, Minn.

[21] Appl. No.: 698,227

[22] Filed: Aug. 14, 1996

Related U.S. Application Data

[63] Continuation of Ser. No. 309,949, Sep. 21, 1994, abandoned.

[51] Int. Cl.$^6$ ................................................. A61M 29/00
[52] U.S. Cl. ........................... 128/772; 128/657; 128/656; 128/658; 604/96
[58] Field of Search .............................. 604/96, 95, 164, 604/165, 280, 283, 264; 128/656–658

[56] References Cited

U.S. PATENT DOCUMENTS

| | | |
|---|---|---|
| 3,358,676 | 12/1967 | Frei et al. |
| 3,674,014 | 7/1972 | Tillander |
| 3,722,505 | 3/1973 | Kolin |
| 3,941,119 | 3/1976 | Corrales |
| 3,961,632 | 6/1976 | Moossun |
| 4,054,128 | 10/1977 | Seufert et al. |
| 4,077,412 | 3/1978 | Moossun |
| 4,134,405 | 1/1979 | Smit |
| 4,162,679 | 7/1979 | Reenstierna |
| 4,244,362 | 1/1981 | Anderson |
| 4,249,536 | 2/1981 | Vega |
| 4,315,509 | 2/1982 | Smit |
| 4,671,287 | 6/1987 | Fiddian-Green |
| 4,784,646 | 11/1988 | Feingold |
| 4,790,809 | 12/1988 | Kuntz |
| 4,804,054 | 2/1989 | Howson et al. |
| 4,809,713 | 3/1989 | Grayzel |
| 4,875,489 | 10/1989 | Messner et al. |
| 4,922,923 | 5/1990 | Gambale et al. |

(List continued on next page.)

FOREIGN PATENT DOCUMENTS

| | | |
|---|---|---|
| 0 416 734 A1 | 7/1990 | European Pat. Off. |
| 0 415 332 A1 | 8/1990 | European Pat. Off. |
| 0 232 968 B1 | 9/1992 | European Pat. Off. |
| WO 89/07958 | 9/1989 | WIPO |
| 9315786 | 2/1993 | WIPO |
| WO 94/03229 | 2/1994 | WIPO |

OTHER PUBLICATIONS

J. Driller, W. Casarella, T. Asch, S.K. Hilal; The POD Bronchial Catheter, IEEE Transactions on Magnetics, vol. Mag–6, No. 2, pp. 353–355, Jun., 1970.

A. Snider; New Techniques Used in Lung Biopsy, The Washington Post, p. E16, Thursday, Dec. 4, 1969.

D. Montgomery and R. Weggel; Magnetic Forces for Medical Applications, IEEE Transcactions on Magnetics, p. 374, Jun. 1970.

D. Montgomery, J. Hale, N. Pierce and S. Yodh; A Magnetically Guided Catheter System for Intracranial Use in Man, IEEE Transactions on Magnetics, pp. 374–375, Jun. 1970.

H. Tillander; Selective Angiography with a Catheter Guided by a Magnet, IEEE Transactions on Magnetics, vol. Mag–6, No. 2, pp. 355–358, Jun. 1970.

Primary Examiner—Gary Jackson
Attorney, Agent, or Firm—Nawrocki, Rooney & Sivertson

[57] ABSTRACT

A catheter configured for use with a guidewire that includes operably connected, magnetically responsive material. The catheter comprises an elongated shaft having a proximal end and a distal end. Magnetically active material is operably connected to the shaft and configured such that the shaft may be magnetically coupled to the guidewire, along a portion of the shaft. The magnetic couple may be sufficiently strong to hold the guidewire and shaft together along a portion of the shaft and a portion of the guidewire while allowing longitudinal sliding of the shaft relative to the guidewire. Rather than connecting the magnetically responsive material to the guidewire and the magnetically active material to the catheter, the magnetically responsive material may be connected to the catheter and the magnetically active material to the guidewire.

28 Claims, 7 Drawing Sheets

U.S. PATENT DOCUMENTS

| | | |
|---|---|---|
| 5,035,686 | 7/1991 | Crittenden et al. . |
| 5,117,838 | 6/1992 | Palmer et al. . |
| 5,156,594 | 10/1992 | Keith . |
| 5,269,759 | 12/1993 | Hernandez et al. .................... 604/96 |
| 5,464,023 | 11/1995 | Viera ....................... 128/772 |
| 5,487,729 | 1/1996 | Avellan et al. .......................... 604/96 |
| 5,492,538 | 2/1996 | Johlin, Jr. .................................. 604/264 |

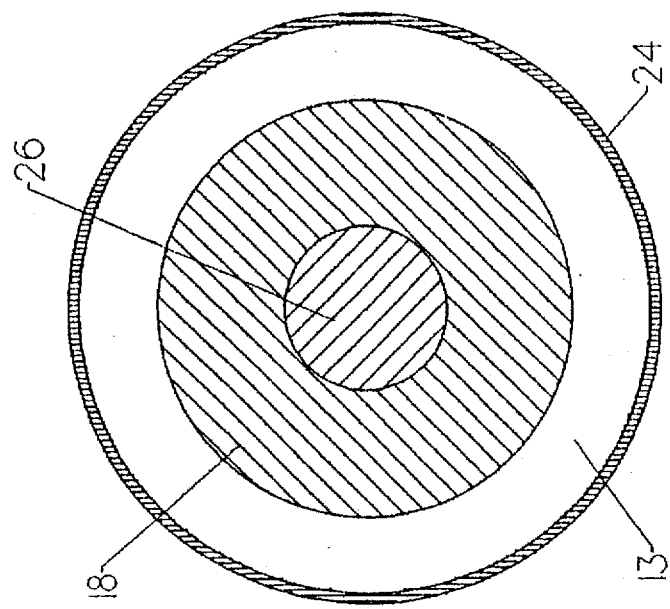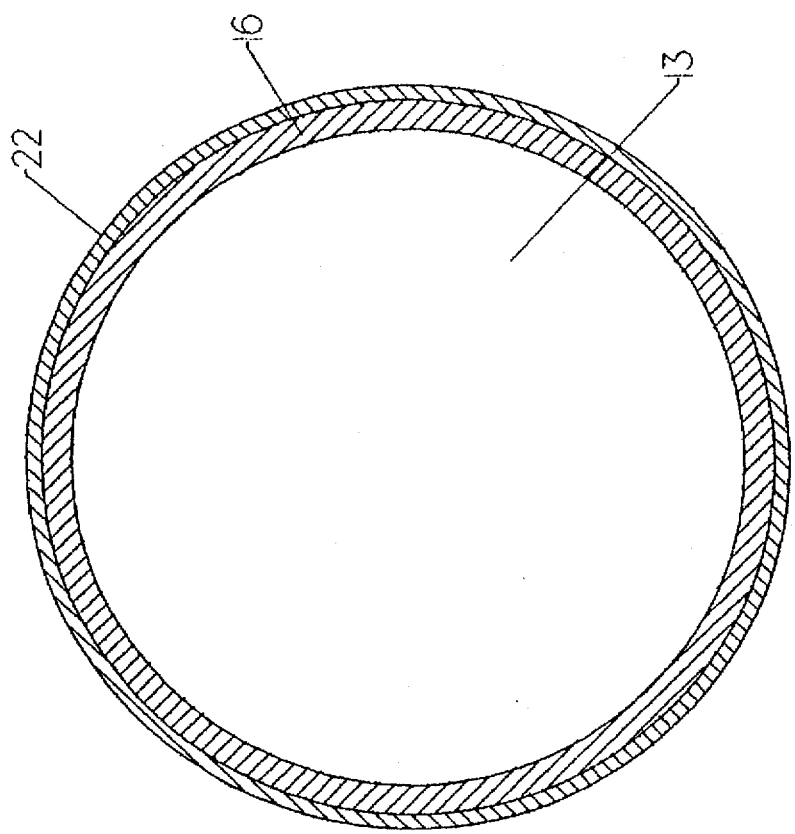

MAGNETIC LUMEN CATHETER

This application is a continuation of application Ser. No. 08/309,949, filed Sep. 21, 1994, now abandoned.

BACKGROUND OF THE INVENTION

The present invention relates to the field of catheterization. In particular, the present invention relates to a catheter guided into a patient preferably along a guidewire.

The invention may find applications in many catheterizations procedures, but it is particularly suitable for angioplasty. Angioplasty is an efficient and effective method for treating many types of vascular diseases. Angioplasty is widely used for opening stenoses or lesions in coronary arteries or other vessels. A dilatation catheter having an inflatable balloon at its distal end is often used to perform angioplasty procedures. Using fluoroscopy, the physician may guide the dilatation catheter through the vascular system until the balloon is positioned across a stenosis. The balloon is then inflated by supplying a fluid under pressure through an inflation lumen to the balloon. Inflation of the balloon causes stretching of the artery and pressing of the lesion into the artery wall to increase the diameter of the arterial lumen and reestablish acceptable blood flow.

Often when performing an angioplasty procedure, prior to inserting a dilatation catheter into a patient's vascular system, the physician will steer a guidewire through the patient's vascular system until the distal end of the guidewire is across the stenosis. Once the guidewire is in place, a path to the stenosis is established over which a dilatation catheter having a through guidewire lumen can readily be advanced to the stenosis.

A "standard" guidewire used in angioplasty is about 150-175 cm long. When the guidewire and catheter are in place across a stenosis in a patient, a portion of the guidewire protrudes proximally from the catheter and outside the patient. The protruding portion enables the guidewire to be manipulated by a physician.

In some instances, it may be desirable to exchange a dilatation catheter already on the guidewire for a second dilatation catheter. It is usually preferred that the catheter be removed in a manner which enables the guidewire to remain in place in the blood vessel across the stenosis. If the guidewire remains in place, the succeeding catheter may be more readily advanced to the stenosis. To maintain the guidewire in place while withdrawing the catheter, the guidewire must be gripped at its proximal end to prevent it from being pulled out of the blood vessel with the catheter. The catheter, however, is usually longer than the proximal portion of the guidewire which protrudes out of the patient. Thus, if the physician were to attempt to fully withdraw the catheter while leaving the guidewire in place, the catheter would completely cover the proximal end of the guidewire and consequently, the physician would no longer be able to grip the guidewire. If the physician can no longer hold the guidewire, the guidewire may shift out of position. The guidewire may shift significantly such that it no longer extends across the stenosis.

To allow the physician to grip the guidewire throughout the catheter exchange, longer exchange guidewires have been developed. These exchange guidewires are usually about 300 cm long, or about 125-150 cm longer than typical "standard" guidewires. The additional length of the exchange guide wire allows for a proximally protruding portion which is longer than the length of the catheter to be removed. When a catheter is removed, some part of the proximally protruding portion of the exchange wire is always exposed to allow the physician to grip some portion of the wire throughout the exchange.

Long exchange guidewires may be cumbersome and difficult to handle. One solution is the use of a guidewire extension which is attached to the proximal end of a "standard" guidewire while the guidewire remains in place across the stenosis. A guidewire extension effectively increases the length of the guidewire to that of an exchange guidewire. The extension need only be attached to a guidewire during a catheter exchange. The extended guidewire may still be cumbersome though, as the physician is required to handle an extended length of the guidewire outside of the patient during at least a portion of the angioplasty procedure.

An alternate way of accomplishing a catheter exchange, while leaving the guidewire in place and without lengthening the guidewire, is to use a balloon catheter with a short guidewire lumen located near the distal end of the catheter. With this configuration, the guidewire is outside the balloon catheter except where the short lumen goes over the wire. This arrangement allows the catheter to be withdrawn over the guidewire without requiring a physician to release the guidewire until the distal end of the catheter is outside of the patient's body. The guidewire lumen of the catheter is shorter than the length of the exposed guidewire which allows at least some portion of the proximal end of the guidewire to be exposed at all times. Consequently, the guidewire may be gripped by the physician and held in position relative to the stenosis during removal of the catheter.

A further way of exchanging a catheter without the use of extended guidewires, is to engage the guidewire at a point distal of the catheter. This has been done by providing an inflatable guidewire holding balloon which is adapted to be inflated within a guide catheter. With this arrangement, the dilatation catheter in the patient is withdrawn over the guidewire and into the guide catheter a short distance. The guidewire holding balloon is aligned distally relative to the dilatation catheter and is inflated, thereby trapping the guidewire against an inner wall of the guide catheter. The dilatation catheter is then withdrawn over the guidewire, the proximal end of the guidewire can be released, and a second dilatation catheter placed on the guidewire and advanced along the guidewire to the point where the guidewire is trapped against the guide catheter wall. The guidewire holding balloon is then deflated and the physician advances the second dilatation catheter along the guidewire to the stenosis. It also has been disclosed that mechanical means such as a wire snare can be used within a guide catheter to secure the guidewire rather than a balloon.

A further way of accomplishing a catheter exchange uses an essentially "standard" guidewire having a magnetically responsive segment connected to its proximal end. After the guidewire has been placed in the patient by the physician, a magnetically active tool is placed adjacent the magnetically responsive material attached to the guidewire to produce a magnetic coupling between the guidewire and the magnetically active tool. The coupling is sufficiently strong to hold the longitudinal position of the guidewire relative to the magnetic tool while a catheter is being slid either on or off over the proximal end of the guidewire. Because the longitudinal position of the guidewire can be maintained while the catheter is slid off or on to the guidewire, catheter exchange may be readily achieved. Physicians, however, may prefer the "feel" of directly gripping the guidewire, rather than having the guidewire held by the magnetic tool.

SUMMARY OF THE INVENTION

The present invention eliminates the need for an extended guidewire. The present invention also however, allows the physician to directly grip the guidewire, rather than having the guidewire held by a magnetic tool or trapping balloon. Although the latter devices are completely acceptable for accomplishing rapid catheter exchanges, some physicians may prefer the "feel" of directly gripping the guidewire. This might be of particular significance to physicians accustomed to using those catheters having a short distally disposed guidewire lumen for performing catheter exchange procedures. Additionally, because the guidewire is not within in a lumen as the catheter is advanced along the guidewire, the friction between the guidewire and catheter may be diminished. The reduced friction between the guidewire and catheter may allow the catheter to be more readily advanced and withdrawn from a vascular lumen. The lack of a guidewire lumen may also allow the catheter to be configured with a narrower profile or lesser diameter than a catheter having a guidewire lumen. A narrower profile can ease advancement and withdrawal of the catheter along the guidewire.

The catheter in accordance with the present invention is preferably for use with a guidewire. In accordance with the present invention, the catheter may be magnetically coupled to the guidewire. In order to magnetically couple the catheter to the guidewire either the catheter includes magnetically active material and the guidewire includes magnetically responsive material, or the catheter includes magnetically responsive material and the guidewire includes magnetically active material. As used herein, the term "magnetically active material" means any material producing a magnetic field, such as a permanent magnet or an electromagnet. The term "magnetically responsive material" means any material attracted to a magnetic field.

Although the present invention could be used with many types of catheters, it is particularly suited for angioplasty, where rapid exchange of dilatation catheters is often desirable. An angioplasty catheter in accordance with the present invention, configured for use with a guidewire may include an elongated shaft having a longitudinally extending inflation lumen, a proximal end and a distal end. An inflatable balloon may be connected at the distal end of the shaft in fluid communication with the inflation lumen. Magnetically active material is operably connected to the shaft and may be configured such that the shaft is magnetically coupled to the guidewire which includes magnetically responsive material operably connected thereto. The guidewire and shaft are preferably magnetically coupled along a portion of the length of the shaft. The magnetic couple is preferably sufficiently strong to hold the guidewire adjacent the shaft, while simultaneously allowing longitudinal sliding of the shaft relative to the guidewire. The magnetically active material may be spaced along a portion of the shaft in continuous or discontinuous segments.

Although the present invention provides a means for coupling a catheter to a guidewire without the need for a guidewire lumen, it is possible to use the present invention with a catheter having a guidewire lumen. Such a configuration could provide additional support for the guidewire on a single operator exchange catheter. In one possible embodiment, the catheter defines a short guidewire lumen proximate its distal end. In such an angioplasty balloon catheter, the short guidewire lumen may be proximal the balloon, distal the balloon or extend through the balloon. With such a configuration the catheter is preferably magnetically coupled along a portion of its length to the guidewire. A remaining portion of the catheter could be physically coupled to the guidewire by insertion of the guidewire into the guidewire lumen.

BRIEF DESCRIPTION OF THE DRAWINGS

FIG. 2 shows a latitudinal cross section of a portion of the angioplasty catheter as shown in FIG. 1;

FIG. 3 shows a latitudinal cross section of another portion of the angioplasty catheter shown in FIG. 1;

DETAILED DESCRIPTION OF THE INVENTION

Figure 1:
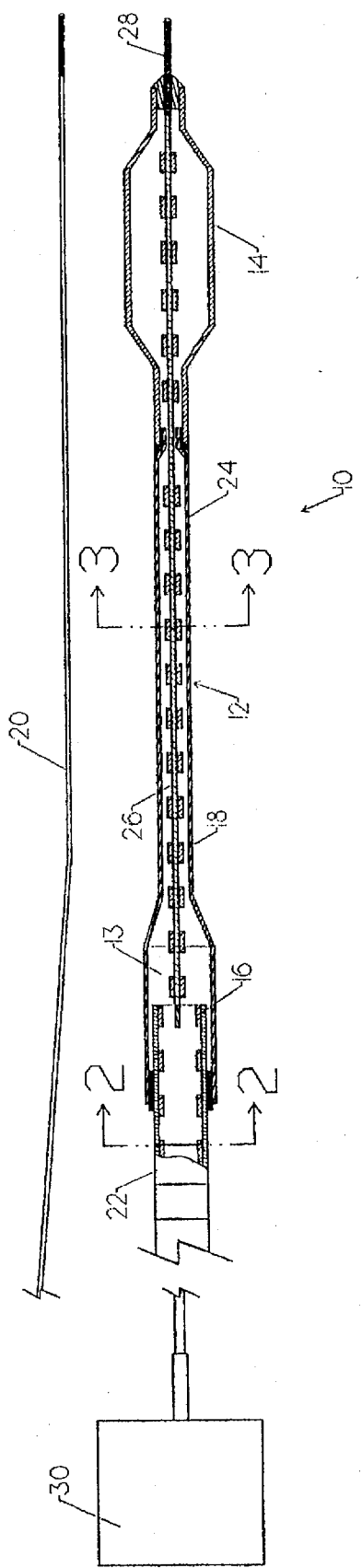
FIG. 1 shows a longitudinal cross section of an angioplasty catheter in accordance with the present invention.

A magnetic lumen catheter in accordance with the present invention is shown in FIG. 1 and generally referred to by the reference numeral 10. Catheter 10 includes a shaft 12 having a proximal end and a distal end. Catheter 10 may be a dilatation catheter including a balloon 14 at the distal end of shaft 12. Shaft 12 defines an inflation lumen 13 in fluid communication with balloon 14. Magnetically active material 16 and 18 may be operably connected to catheter 10 along a portion of its length. FIG. 1 also shows a guidewire 20 including magnetically responsive material. For angioplasty procedures, guidewire 20 is preferably approximately the length of a "standard" guidewire, that is, approximately 150–175 cm. When catheter 10 and guidewire 20 are placed together, magnetically active material 16 and/or 18 and the magnetically responsive material of guidewire 20 interact to magnetically coupled catheter 10 to guidewire 20. The magnetic couple may be sufficiently strong to hold guidewire 20 adjacent catheter 10 along a portion of catheter 10 and guidewire 20 while allowing longitudinal sliding of catheter 10 relative to guidewire 20.

The ability to slide catheter 10 relative to guidewire 20 while magnetically coupled, allows physicians to directly grip the guidewire while performing catheter exchanges without using an extension guidewire. Further, the guidewire need not be indirectly held by a magnetic tool or trapping balloon during catheter exchanges. Although the latter devices are completely acceptable for accomplishing rapid catheter exchanges, some physicians may prefer the "feel" of directly gripping the guidewire. This might be of particular significance to physicians accustomed to accomplishing those catheter exchanges with a catheter having a short distally disposed guidewire lumen.

As used herein, the term "magnetically active material" means any material producing a magnetic field, such as a permanent magnet or electromagnet. The meaning of "magnetically responsive material" is any material attracted to the magnetic field produced by a magnetically active material.

In one embodiment of the invention, as shown in FIG. 1, shaft 12 includes a proximal tubular portion 22 and a distal tubular portion 24. Proximal tubular portion 22 may be a stainless steel hypotube or any other type of tube commonly used in the construction of angioplasty catheters. Distal tube 24 may be a polymer tube which can be more flexible than proximal tube 22. The distal end of proximal tube 22 may be connected to the proximal end of tube 24 by adhesive or any other means well known to those skilled in the art. Likewise, the distal end of distal tube 24 may be connected to balloon 14 by adhesive or any other means as well known to those skilled in the art.

A core wire 26 may be connected to the distal end of proximal tube 22 by braising or other suitable means well known to those skilled in the art. Core wire 26 extends distally through distal tube 24 and through balloon 14. The distal end of the balloon core wire 26 may be connected to a coil 28 which can extend beyond the distal end of the balloon.

In one embodiment of the invention, as shown in FIGS. 1 and 2, magnetically active material 16 may be configured in a cylindrical shape and placed concentrically within proximal tube 22. The cylinder defined by magnetically active material 16 may be hollow to avoid complete obstruction of inflation lumen 13. Magnetically active material 16 may be connected to proximal tube 22 by suitable adhesive or any other means well known to those skilled in the art. Alternate configurations of magnetically active material are considered to be readily apparent for example, material 16 may be connected to the exterior of tube 22 or embedded in tube 22. Material 16 might be semi-circular or longitudinally extending strips.

FIGS. 1 and 3 show an alternate way to connect magnetically active material to catheter 10. In this case, magnetically active material 18 is connected to core wire 26 by suitable adhesive or other means well known to those skilled in the art. Material 18 is formed in a cylindrical shape having an outside diameter less than the inside diameter of inflation lumen 13. This allows inflation fluid to move with limited obstruction through lumen 13. It is readily apparent that many configurations of the magnetically active material are possible, for example, that magnetically active material may be close to one side or asymmetrically attached to core wire 26. Material 18 might also be semi-circular or longitudinally extending strips.

Magnetically active material 16 and 18 may be permanent magnets or electromagnets controlled by a suitable power source control 30. It is also envisioned that magnetically responsive material may be substituted for magnetically active material 16 and 18 and guidewire 20 may include magnetically active material. The magnetically active material in guidewire 20 may create a magnetic field to couple catheter 10 to guidewire 20.

Figure 4:
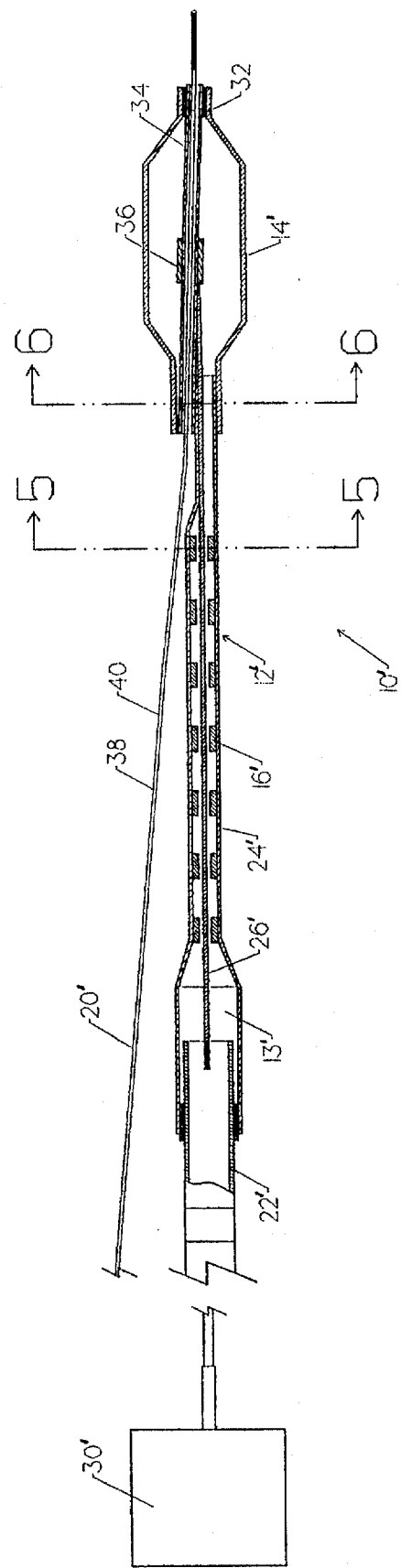
FIG. 4 shows a longitudinal cross section of an alternate embodiment of the angioplasty catheter in accordance with the present invention.

FIG. 4 shows an alternate embodiment of a catheter made in accordance with the present invention generally referred to by reference number 10'. Catheter 10' is distinguished from catheter 10 by the inclusion of a guidewire lumen 32. Lumen 32 can provide additional support to the guidewire similar to an over-the-wire catheter. Like catheter 10, catheter 10' includes magnetically active material 16' for coupling catheter 10' to guidewire 20'. It can be appreciated that the magnetically active material connected to catheter 10' could be configured in any of the ways discussed above with respect to catheter 10.

Catheter 10' may include a shaft 12' formed from a proximal tube 22' and a distal tube 24'. Shaft 12' may define an inflation lumen 13' therethrough. The distal end of proximal tube 22' may be connected to the proximal end of distal tube 24' and a balloon 14' may be connected to the distal end of distal tube 24'. A core wire 26' may be connected to the distal end of proximal tube 22' and extend through distal tube 24' to balloon 14'. It can be appreciated that catheter 10' may not include core wire 26. Longitudinal forces may be transferred along guidewire 20' and/or distal shaft 24', rather than core wire 26'. A short tube 34 may be connected to distal tube 24' and/or core wire 26'. Tube 34 may define guidewire lumen 32. A radiopaque marker band 36 may also be connected at the distal end of core wire 26'.

Figure 6:
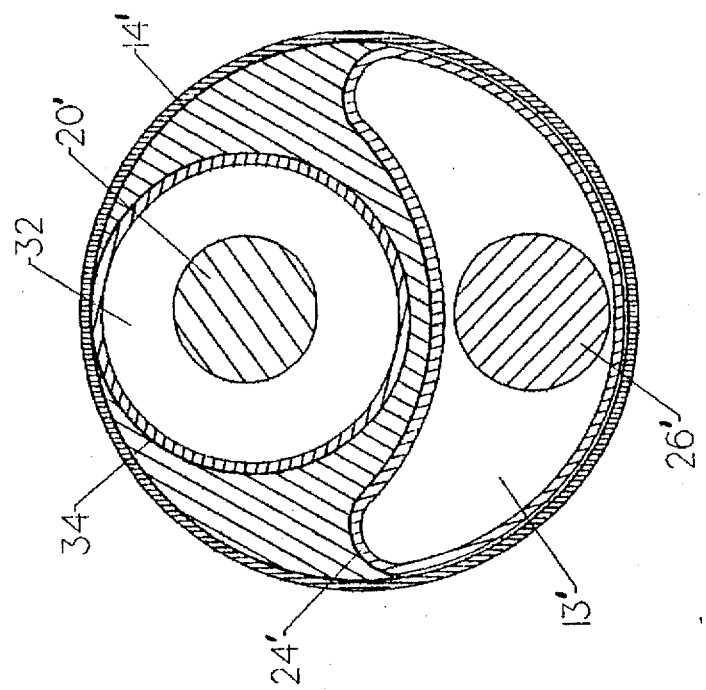
FIG. 6 shows a latitudinal cross section of another portion of the angioplasty catheter shown in FIG. 4.
Figure 5:
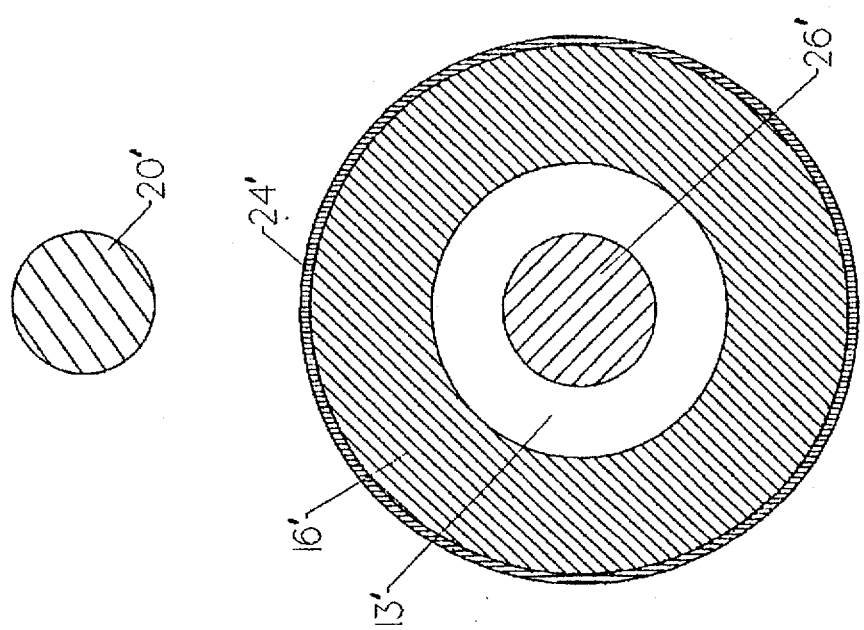
FIG. 5 shows a latitudinal cross section of a portion of the angioplasty catheter shown in FIG. 4.

As shown in FIG. 5 magnetically active material 16' may be cylindrically shaped, corresponding in shape to the inside of distal tube 24'. The cylinder defined by magnetically active material 16' may be hollow and have an internal diameter greater than the external diameter of core wire 26' to allow passage of inflation fluid through inflation lumen 13'. FIGS. 4 and 6 show one possible configuration of inflation lumen 13' and guidewire lumen 32'.

Magnetically active material 16' may be a permanent magnet or an electromagnet controlled by power source control 30'. Alternately, material 16' may be magnetically responsive material attracted to magnetically active material present in guidewire 20'. The material present in guidewire 20' may likewise be a permanent magnet or electromagnet.

As shown in FIG. 4, guidewire 20' may have alternating regions of magnetically active material 38 and magnetically responsive material 40. For example, magnetically active material 38 and magnetically responsive material 40 may be placed in longitudinally alternating bands around guidewire 20'. It should be noted that either guidewire 20 or 20' may be used with catheter 10 or 10'.

Figure 7:
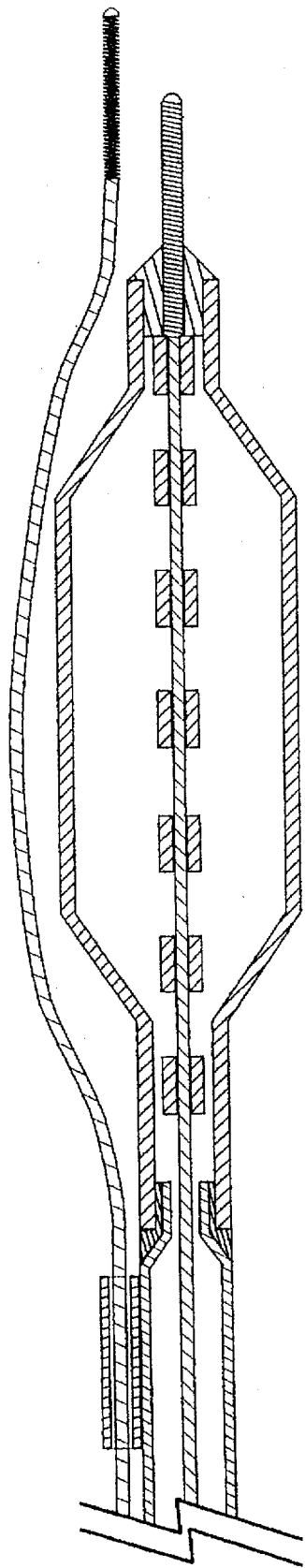
FIG. 7 shows a longitudinal cross section of a second alternate embodiment of the angioplasty catheter in accordance with the present invention.

FIG. 7 shows a longitudinal cross section of a second alternate embodiment of the catheter made in accordance with the present invention generally referred to by reference numeral 10". Like catheter 10', catheter 10" includes a guidewire lumen 32" and magnetically active material 16" for coupling catheter 10" to a guidewire 20". Catheter 10" includes a shaft 12". Shaft 12" may define an inflation lumen 13". A core wire 26" may extend through a portion of shaft 12" and through a balloon 14". A short tube 34" can be connected to shaft 12" proximally of balloon 14'. Tube 34" can define the guidewire lumen 32". Placing lumen 32" proximally of the balloon provides additional support to guidewire 20", while retaining a compact latitudinal cross section or profile distally of the balloon.

The distribution and placement of magnetically responsive and magnetically active materials within or on catheter 10" and 20" may be the same as discussed above with respect to catheters 10 and 10' and guidewires 20 and 20'.

Figure 8:
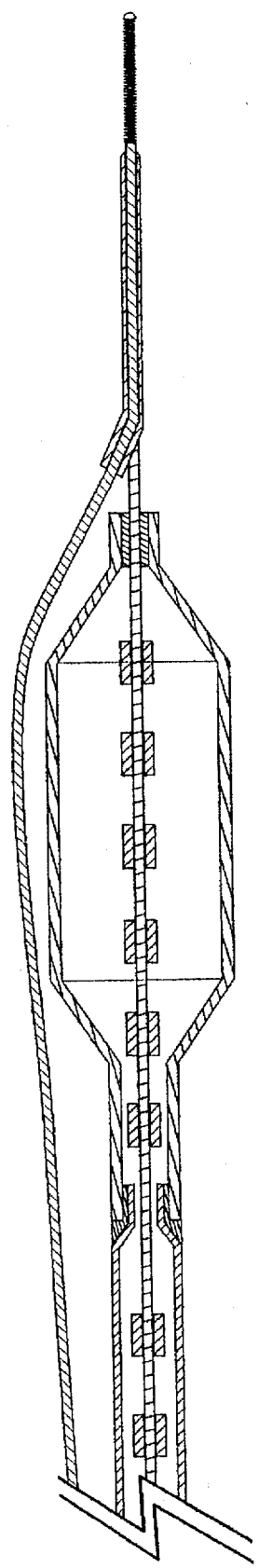
FIG. 8 shows a third alternate embodiment of the angioplasty catheter in accordance with the present invention.

FIG. 8 shows a longitudinal cross section of a third alternate embodiment of a catheter 10'" in accordance with the present invention. Catheter 10'" includes a shaft 12'" and an inflatable balloon 14'" connected to the distal end of shaft 12'". Shaft 12'" may define an inflation lumen 13'". A core wire 26'" may extend through a portion of shaft 12'" and through balloon 14'". A guidewire lumen 32'" may be disposed distally of balloon 14'". Lumen 32'" may be defined by a tube 34'" connected to shaft 26'". Catheter 10'" may include magnetically active material 16'" to couple catheter 10'" to a guidewire 20'". The distribution and placement of the magnetically responsive and magnetically active materials within catheter 10'" and 20'" may be the same as discussed above with respect to catheters 10 and 10' and guidewires 20 and 20'.

Figure 9:
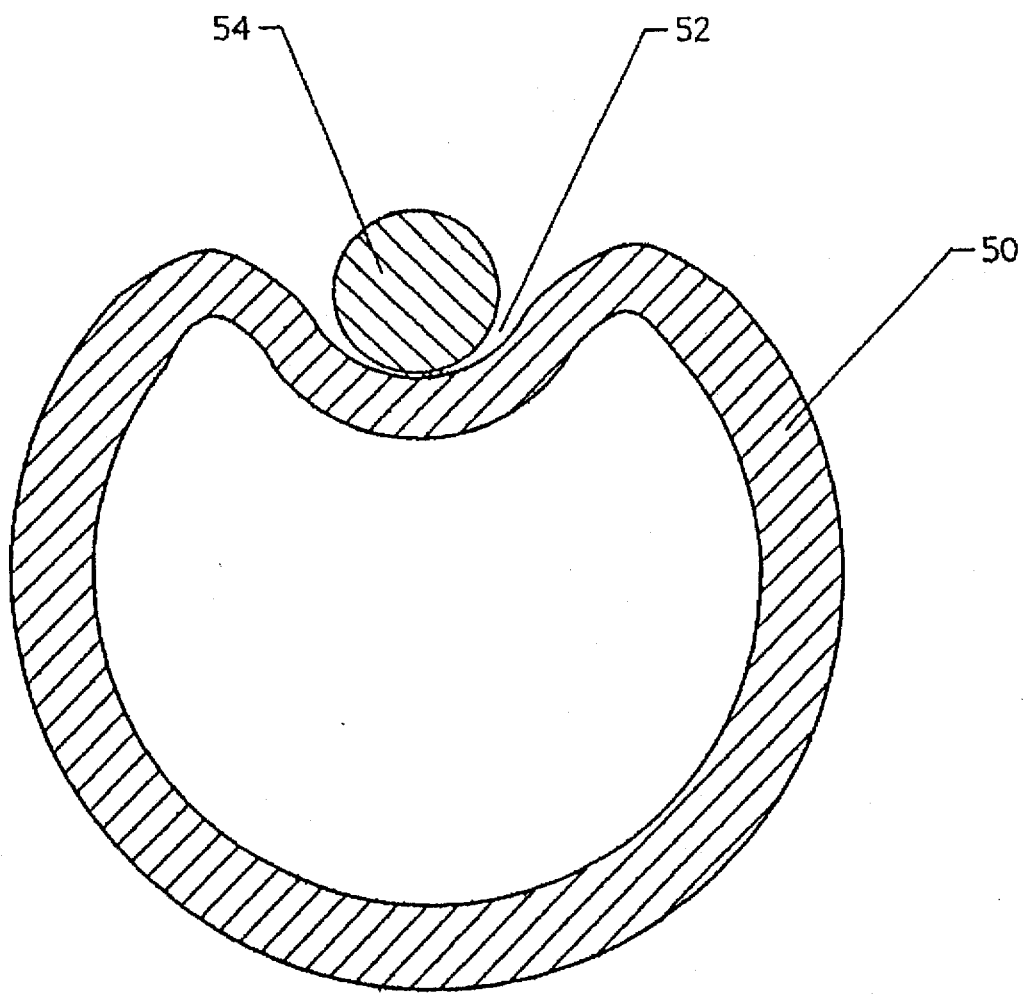
FIG. 9 shows the latitudinal cross section of a catheter in accordance with the present invention including a guidewire channel.

FIG. 9 shows a latitudinal cross section of a shaft 50 of a catheter in accordance with the present invention. Shaft 50 includes a guidewire channel 52 which extends longitudinal along a portion of shaft 50. As shown in FIG. 9 a guidewire 54 may be placed within guidewire channel 52 rather than a guidewire lumen. By placing guidewire 54 in channel 52, it is less likely that guidewire 54 will be pinched between shaft 50 and the wall of a vessel when guidewire 54 is not in a guidewire lumen. It is anticipated that channel 52 may be incorporated into shafts 12, 12', 12" and 12'" for the related guidewires described above. Channels may also be used in place of guidewire lumens 32" and 32'" shown in FIGS. 7 and 8, respectively. It is also anticipated that the balloons described above may have a longitudinally extending guidewire channels similar to channels 52.

In discussing the use of the catheters and guidewires disclosed above, reference will be made to catheter 10 and guidewire 20, except where reference to alternate embodiments of the catheter and guidewire is helpful to illustrate the particular advantages of the alternate embodiments. When performing a typical angioplasty procedure with the catheters and guidewires made in accordance with the present invention, guidewire 20 is advanced into a vascular lumen and across a stenosis or lesion. Catheter 10 will be placed adjacent guidewire 20 to magnetically couple catheter 10 to guidewire 20. Then guidewire 20 can be held in place while catheter 10 is advanced proximally toward the lesion along guidewire 20. Catheter 10 remains magnetically coupled to guidewire 20. It is also possible to advance catheter 10 and guidewire 20 simultaneously.

If the physician desires to exchange catheter 10 for a similar catheter having for example, a large diameter balloon, guidewire 20 may be gripped by the physician to hold it in place while catheter 10 remains magnetically coupled to guidewire 20 and is withdrawn distally from the vascular lumen. The next catheter is advanced along guidewire 20 in the same manner as catheter 10.

Catheters 10', 10" and 10'" may be advanced, withdrawn and exchanged in a manner similar to catheter 10. However, when advancing a catheter having a guidewire lumen such as catheter 10', the proximal end of guidewire 20' is first inserted into the distal end of guidewire lumen 32. Then guidewire 20' is placed alongside or magnetically coupled to a remaining portion of catheter 10'.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter configured for use with a guidewire, the guidewire including operably connected, magnetically responsive material, the catheter comprising:
   an elongated shaft having a proximal portion and a distal portion, the distal portion having a distal end;
   a balloon connected at the distal end of the shaft; and
   magnetically active material means, operably connected to the distal portion of the shaft, for creating a magnetic couple between the magnetically responsive material on the guidewire and a portion of the shaft including the magnetically active material means, wherein the magnetic couple is sufficiently strong to hold the guidewire and shaft together along a portion of the shaft and a portion of the guidewire while allowing longitudinal sliding of the shaft relative to the guidewire.

2. A catheter in accordance with claim 1, wherein a portion of the catheter defines a guidewire lumen.

3. A catheter in accordance with claim 1, wherein the magnetically active material is spaced along the portion of the shaft in discontinuous segments.

4. A catheter in accordance with claim 1, wherein a portion of the catheter defines a guidewire channel.

5. A catheter in accordance with claim 1, wherein the magnetically active material is a permanent magnet.

6. A catheter in accordance with claim 1, wherein the magnetically active material is an electromagnet.

7. A catheter in accordance with claim 1, wherein the magnetically active material is a permanent magnet.

8. A catheter in accordance with claim 1, wherein the magnetically active material is an electromagnet.

9. An angioplasty catheter configured for use with a guidewire, the guidewire including operably connected magnetically responsive material, the catheter comprising:
   an elongated shaft having a longitudinally extending inflation lumen, a proximal portion and a distal portion, the distal portion having a distal end;
   an inflatable balloon connected at the distal end of the shaft and in fluid communication with the inflation lumen; and
   magnetically active material means, operably connected to the distal portion of the shaft, for creating a magnetic couple between the magnetically responsive material on the guidewire and a portion of the shaft including the magnetically active material means wherein the magnetic couple is sufficiently strong to hold the guidewire and shaft together along a portion of the shaft and a portion of the guidewire while allowing longitudinal sliding of the shaft relative to the guidewire.

10. A catheter in accordance with claim 9, wherein the magnetically active material is disposed within the inflation lumen.

11. A catheter in accordance with claim 10, wherein the magnetically active material has a generally cylindrical shape corresponding generally to the shape of the inflation lumen and the magnetically active material defines at least one through passage in fluid communication with the inflation lumen.

12. A catheter in accordance with claim 11, wherein magnetically active material is spaced along a portion of the shaft in discontinuous segments.

13. A catheter in accordance with claim 9, wherein the shaft includes a proximal hypotube defining a first portion of the inflation lumen and a distal polymer tube defining a second portion of the inflation lumen, the proximal tube being connected to the distal tube and the distal tube being connected to the balloon such that the first and second portions of the inflation lumen are in fluid communication with each other and the balloon.

14. A catheter in accordance with claim 13, further comprising a core wire operably connected to the distal end of the hypotube and extending distally through the portion of the inflation lumen defined by the distal tube and into the balloon, and the magnetically active material being operably connected to the core wire.

15. A catheter in accordance with claim 14, wherein the magnetically active material is spaced along a portion of the core wire in discontinuous segments.

16. A catheter in accordance with claim 9, further comprising a guidewire lumen.

17. A catheter in accordance with claim 16, wherein the guidewire lumen is disposed proximally of the balloon.

18. A catheter in accordance with claim 16, wherein the guidewire lumen is disposed through the balloon.

19. A catheter in accordance with claim 16, wherein the guidewire lumen is disposed distally of the balloon.

20. A catheter in accordance with claim 9, wherein a portion of the catheter defines a guidewire channel.

21. A magnetic lumen catheter system, comprising:

a guidewire including operably connected, magnetically responsive material;

an elongated catheter including a shaft having a proximal portion and a distal portion having a distal end, and an operative element at the distal end; and magnetically active material operably connected to the distal portion of the shaft and configured such that the shaft may be magnetically coupled to the guidewire, along a portion of the shaft.

22. A catheter system in accordance with claim 21, wherein the magnetically responsive material is spaced along a portion of the guidewire in discontinuous segments.

23. A catheter system in accordance with claim 21, wherein the magnetically active material is a permanent magnet.

24. A catheter system in accordance with claim 21, wherein the magnetically active material is an electromagnet.

25. A catheter configured for use with a guidewire, the guidewire including operably connected, magnetically active material, the catheter comprising:

an elongated shaft having a proximal portion and a distal portion having a distal end, and an operative element at the distal end; and magnetically responsive material means, operably connected to the distal portion of the shaft, for creating a magnetic couple between the magnetically active material on the guidewire and a portion of the shaft including the magnetically responsive material means wherein the magnetic couple is sufficiently strong to hold the guidewire and shaft together along a portion of the shaft and a portion of the guidewire while allowing longitudinal sliding of the shaft relative to the guidewire.

26. A catheter in accordance with claim 25, wherein a portion of the catheter defines a guidewire lumen.

27. A catheter in accordance with claim 25, wherein the magnetically responsive material is spaced along the portion of the shaft in discontinuous segments.

28. A catheter in accordance with claim 25, wherein a portion of the catheter defines the guidewire channel.

* * * * *